(12) United States Patent  
Cleverdon et al.

(10) Patent No.: US 8,921,636 B2  
(45) Date of Patent: Dec. 30, 2014

(54) CONVERSION OF HF ALKYLATION UNITS FOR IONIC LIQUID CATALYZED ALKYLATION PROCESSES

(75) Inventors: Robert Fletcher Cleverdon, Walnut Creek, CA (US); Christine Marie Phillips, Pleasant Hill, CA (US); Hye Kyung Cho Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 277 days.

(21) Appl. No.: 13/230,774

(22) Filed: Sep. 12, 2011

(65) Prior Publication Data

US 2013/0066133 A1    Mar. 14, 2013

(51) Int. Cl.
| | | |
|---|---|---|
| C07C 2/58 | (2006.01) | |
| C07C 2/64 | (2006.01) | |
| C07C 7/144 | (2006.01) | |
| B01J 19/00 | (2006.01) | |
| B01J 38/56 | (2006.01) | |

(52) U.S. Cl.
CPC . B01J 19/00 (2013.01); C07C 2/58 (2013.01); C07C 2531/02 (2013.01); C07C 2531/14 (2013.01); B01J 2219/00006 (2013.01); B01J 2219/00047 (2013.01)
USPC ........... 585/721; 585/446; 585/818; 422/187; 502/31

(58) Field of Classification Search
USPC ....................................................... 585/721
See application file for complete search history.

(56) References Cited

U.S. PATENT DOCUMENTS

| 5,284,990 A | 2/1994 | Peterson et al. |
|---|---|---|
| 6,955,793 B1 * | 10/2005 | Arencibia, Jr. ............... 422/202 |
| 7,432,408 B2 * | 10/2008 | Timken et al. ............... 585/709 |
| 7,572,943 B2 | 8/2009 | Elomari et al. |
| 2004/0133056 A1 | 7/2004 | Liu et al. |
| 2008/0142413 A1 | 6/2008 | Harris et al. |

FOREIGN PATENT DOCUMENTS

| WO | WO 2011/015662 A2 * | 2/2011 |
|---|---|---|
| WO | WO2011015662 | 2/2011 |
| WO | WO2011015664 | 2/2011 |

OTHER PUBLICATIONS

Liu et al., "Ionic liquid alkylation process produces high-quality gasoline," *Oil & Gas Journal*, 2006, vol. 104, Issue 40.

PCT International Search Report, PCT/US/2012/032127, filed Apr. 4, 2012, Mail Date: Mar. 21, 2013.

* cited by examiner

*Primary Examiner* — In Suk Bullock
*Assistant Examiner* — Youngsul Jeong
(74) *Attorney, Agent, or Firm* — Steven H. Roth (57) ABSTRACT

Methods for converting an HF alkylation unit to an ionic liquid alkylation system configured for performing ionic liquid catalyzed alkylation processes may comprise connecting at least one component configured for ionic liquid catalyzed alkylation to at least one component of the HF alkylation unit, wherein the at least one component of the HF alkylation unit is retained, modified or adapted for use in the ionic liquid alkylation system. An ionic liquid alkylation system derived from an existing or prior HF alkylation unit is also disclosed.

16 Claims, 2 Drawing Sheets

CONVERSION OF HF ALKYLATION UNITS FOR IONIC LIQUID CATALYZED ALKYLATION PROCESSES

TECHNICAL FIELD

The present invention relates to the conversion of HF alkylation units for ionic liquid catalyzed alkylation processes.

BACKGROUND

Hydrofluoric acid (HF) is used as a catalyst in conventional industrial processes to perform reactions such as aromatic and olefin alkylation, including refinery processes for the production of high-octane gasoline, distillate, and lubricating base oil. The hazards of HF, e.g., related to HF volatility, are well documented. The use of additives to reduce HF volatility is expensive and does not eliminate the need for large quantities of HF in the plant. Meanwhile, efforts to develop safer, alternative catalysts have encountered serious challenges. The conversion of HF alkylation units to use sulfuric acid ($H_2SO_4$) as catalyst requires significant added capital and operating expense, and at the same time introduces the hazards associated with highly corrosive concentrated $H_2SO_4$. Further, solid alkylation catalysts have proved difficult to commercialize due to rapid fouling and deactivation.

Figure 1A:
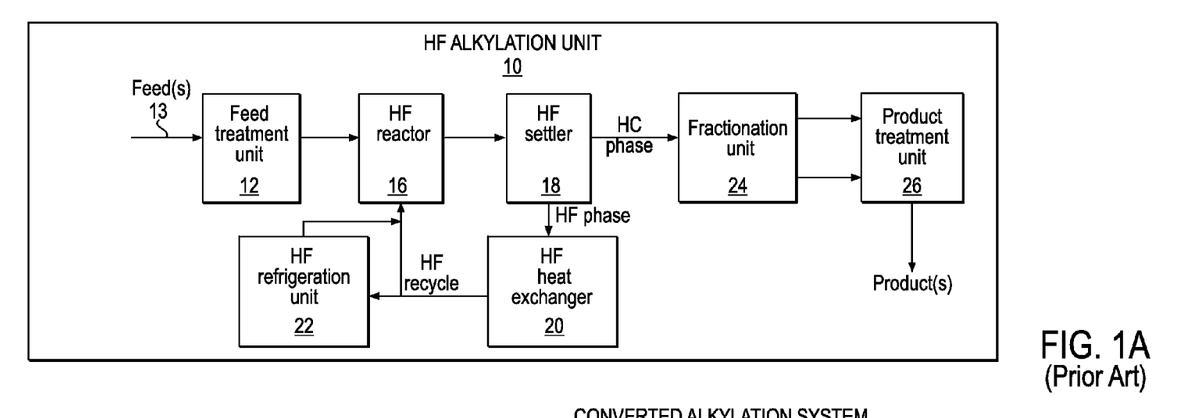
FIG. 1 is a block diagram schematically representing a hydrofluoric acid (HF) alkylation unit, according to the prior art.

FIG. 1 is a block diagram schematically representing an HF alkylation unit 10, according to the prior art. HF alkylation unit 10 may include a hydrocarbon feed line 13, an HF alkylation reactor 16 containing hydrocarbon injection nozzles, and an HF settler 18 coupled to HF reactor 16 for separating an HF/hydrocarbon mixture into a hydrocarbon phase and an HF phase. The HF phase may be recycled to HF reactor 16 via an HF heat exchanger 20. In a more compact design, the heat exchanger could be located inside the HF reactor.

A portion of the HF is sent to an HF regeneration unit 22, then the regenerated HF is combined with the HF recycle stream. Unit 10 may further include a fractionation unit 24 for fractionating the hydrocarbon phase, and a product treatment unit 26 for treating cuts from fractionation unit 24 to provide one or more products. In some instances, a prior art HF alkylation unit may include a feed treatment unit 12 for treating the hydrocarbon feed(s) to HF reactor 16.

U.S. Pat. No. 5,284,990 to Peterson et al. discloses a method for converting an HF alkylation unit to a $H_2SO_4$ alkylation unit. The disclosure of the '990 patent is incorporated by reference herein in its entirety for all purposes.

The quest for an alternative catalytic system to replace conventional HF and $H_2SO_4$ catalysts in alkylation processes has been researched by various groups in both academic and industrial institutions. Thus far, no viable replacement catalyst for performing such processes has been commercialized.

Recently there has been considerable interest in metal halide ionic liquid catalysts as alternatives to HF and $H_2SO_4$ catalysts. As an example, the ionic liquid catalyzed alkylation of isoparaffins with olefins is disclosed in U.S. Pat. No. 7,432,408 to Timken, et al. Further, U.S. Pat. No. 7,572,943 to Elomari, et al. discloses the ionic liquid catalyzed oligomerization of olefins and the alkylation of the resulting oligomers(s) with isoparaffins to produce alkylated olefin oligomers.

PCT Publication No. WO 2011/015664 discloses a method for revamping an HF or $H_2SO_4$ alkylation unit to an ionic liquid alkylation unit, wherein one or more cyclone units are provided to promote the separation of ionic liquid from hydrocarbons.

Liu et al. (*Oil & Gas Journal* (2006) Vol. 104, Issue 40) describe retrofitting an $H_2SO_4$ alkylation unit for use in composite ionic liquid catalyzed alkylation by modifying the settler internals to enhance the separation of the composite ionic liquid from alkylate gasoline, and by providing a surge tank, wherein the composite ionic liquid is recycled from the surge tank to a STRATCO® (continuous stirred tank) reactor.

There is a need for the efficient and cost-effective conversion of existing HF alkylation units into ionic liquid alkylation systems suitable for ionic liquid catalyzed alkylation processes.

SUMMARY

In an embodiment of the present invention there is provided a method for converting an HF alkylation unit to an ionic liquid alkylation system, the method comprising providing an ionic liquid specific sub-system comprising an ionic liquid alkylation reactor; and connecting at least one component of the ionic liquid specific sub-system to at least one component of the HF alkylation unit.

In another embodiment, there is provided a method for converting an HF alkylation unit to an ionic liquid alkylation system, the HF alkylation unit including a fractionation unit, and the method comprises providing an ionic liquid alkylation reactor and an ionic liquid coalescer, connecting the ionic liquid alkylation reactor to at least one hydrocarbon feed line for feeding at least one hydrocarbon feed to the ionic liquid alkylation reactor, and connecting the ionic liquid coalescer to the fractionation unit.

According to a further embodiment, there is provided a method for converting an HF alkylation unit to an ionic liquid alkylation system, the HF alkylation unit including a fractionation unit, and the method comprising providing an ionic liquid alkylation reactor configured for ionic liquid catalyzed alkylation reactions, the ionic liquid alkylation reactor having an ionic liquid/hydrocarbon injection unit in fluid communication therewith; connecting at least one hydrocarbon feed line to the ionic liquid/hydrocarbon injection unit for feeding at least one hydrocarbon feed to the ionic liquid alkylation reactor; providing an ionic liquid/hydrocarbon separation unit; connecting the ionic liquid/hydrocarbon separation unit to the ionic liquid alkylation reactor, wherein the ionic liquid/hydrocarbon separation unit is configured for separating an alkylation reactor effluent of the ionic liquid alkylation reactor into an ionic liquid phase comprising an ionic liquid catalyst and a hydrocarbon phase comprising alkylate; and connecting the ionic liquid/hydrocarbon separation unit to the fractionation unit for feeding at least a portion of the hydrocarbon phase to the fractionation unit.

In still a further embodiment, there is provided an ionic liquid alkylation system derived from an existing HF unit having a fractionation unit, the ionic liquid alkylation system comprising an ionic liquid alkylation reactor configured for ionic liquid catalyzed alkylation reactions; an ionic liquid/hydrocarbon separation unit in fluid communication with the ionic liquid alkylation reactor, wherein the ionic liquid/hydrocarbon separation unit is configured for separating an alkylation reactor effluent of the ionic liquid alkylation reactor into a hydrocarbon phase and an ionic liquid phase; and the ionic liquid alkylation system further comprises the fractionation unit, wherein the fractionation unit is in fluid communication with the ionic liquid/hydrocarbon separation unit.

As used herein, the terms "comprising" and "comprises" mean the inclusion of named elements or steps that are identified following those terms, but not necessarily excluding other unnamed elements or steps.

DETAILED DESCRIPTION

Ionic liquid catalysts may be useful for a range of hydrocarbon conversion reactions, including alkylation reactions for the production of alkylate gasoline blending components, distillate, lubricants, and the like. Conventional HF alkylation units, per se, are not suitable for performing ionic liquid catalyzed alkylation processes. However, according to embodiments of the present invention, one or more components of a conventional HF alkylation unit may be used, or adapted for use, in ionic liquid alkylation systems and processes.

In an embodiment, the present invention provides methods for converting existing HF alkylation units into ionic liquid alkylation systems configured for efficiently performing ionic liquid catalyzed alkylation processes. Such plant conversions may be highly cost-effective during the commercialization of ionic liquid catalyzed alkylation processes. In another embodiment, there is provided an ionic liquid alkylation system derived from a conventional, existing or prior HF alkylation unit.

The disclosure of the commonly assigned U.S. patent application entitled "Conversion of sulfuric acid alkylation units for ionic liquid catalyzed alkylation processes," filed on even date herewith, is incorporated by reference herein in its entirety.

Feedstocks for Ionic Liquid Catalyzed Processes

In an embodiment, feeds for ionic liquid catalyzed hydrocarbon conversion processes may comprise various streams in a petroleum refinery, a gas-to-liquid conversion plant, a coal-to-liquid conversion plant, or in naphtha crackers, middle distillate crackers, or wax crackers, including FCC off-gas, FCC light naphtha, coker off-gas, coker naphtha, hydrocracker naphtha, and the like. In an embodiment, such streams may contain isoparaffin(s) and/or olefin(s).

Examples of olefin containing streams include FCC off-gas, coker gas, olefin metathesis unit off-gas, polyolefin gasoline unit off-gas, methanol to olefin unit off-gas, FCC light naphtha, coker light naphtha, Fischer-Tropsch unit condensate, and cracked naphtha. Some olefin containing streams may contain two or more olefins selected from ethylene, propylene, butylenes, pentenes, and up to $C_{10}$ olefins. Such olefin containing streams are further described, for example, in U.S. Pat. No. 7,572,943, the disclosure of which is incorporated by reference herein in its entirety.

Examples of isoparaffin containing streams include, but are not limited to, FCC naphtha, hydrocracker naphtha, coker naphtha, Fisher-Tropsch unit condensate, and cracked naphtha. Such streams may comprise a mixture of two or more isoparaffins. In a sub-embodiment, an isoparaffin feed for an ionic liquid catalyzed process may comprise isobutane, which may be obtained, for example, from a hydrocracking unit, a butane isomerization unit, or may be purchased.

In an embodiment, olefins and isoparaffins in the feed(s) may participate in ionic liquid catalyzed isoparaffin-olefin alkylation reactions. In another embodiment, olefins in the feed(s) may undergo oligomerization when contacted with an ionic liquid catalyst in a hydrocarbon conversion reactor. Ionic liquid catalyzed olefin oligomerization may take place under the same or similar conditions as ionic liquid catalyzed olefin-isoparaffin alkylation. Ionic liquid catalyzed olefin oligomerization and olefin-isoparaffin alkylation are disclosed, for example, in commonly assigned U.S. Pat. Nos. 7,572,943 and 7,576,252, both to Elomari, et al., the disclosures of which are incorporated by reference herein in their entirety.

Methods for Converting an HF Alkylation Unit into an Ionic Liquid Alkylation System A conventional HF alkylation unit is schematically represented in FIG. 1, supra. Such an existing or prior HF alkylation unit may include, inter alia, an HF reactor, an HF settler disposed downstream from the HF reactor, and a fractionation unit disposed downstream from the HF settler. For various reasons, e.g., due to differences in the physical and chemical properties of the ionic liquid catalyst, the optimum process conditions in the alkylation reactor and the process requirements for ionic liquid catalyzed alkylation, conventional HF alkylation units, per se, are unsuitable for the commercialization of ionic liquid catalyzed alkylation processes. However, an existing HF alkylation unit may be converted into an ionic liquid catalyst alkylation system configured for effectively performing ionic liquid catalyzed alkylation processes. The ionic liquid catalyst alkylation system may also be referred to herein as an ionic liquid alkylation system.

The conversion of an existing or prior HF alkylation unit to an ionic liquid (IL) alkylation system may be referred to herein as an "HF/IL conversion." Such conversions may be realized, for example, by replacing and/or disconnecting one or more components of an HF alkylation unit, by adapting one or more components of the HF alkylation unit for ionic liquid catalyzed alkylation processes, and/or by connecting one or more components of an ionic liquid alkylation system to one or more components of the HF alkylation unit. During an HF/IL conversion, one or more components of an HF alkylation unit may be disconnected, for example, by closing one or more valves, and/or by removing, capping, or replacing one or more lines or interconnections between two or more HF alkylation unit components.

In an embodiment, a method for converting an HF alkylation unit to an ionic liquid alkylation system may comprise providing an ionic liquid catalyst specific sub-system. The ionic liquid catalyst specific sub-system may also be referred to herein as an ionic liquid specific sub-system. Such an ionic liquid specific sub-system may comprise one or more components configured for connection to one or more components of the HF alkylation unit; and the method for HF/IL conversion may further comprise connecting at least one component of the ionic liquid specific sub-system to at least one component of the HF alkylation unit. In an embodiment, one or more components of the ionic liquid specific sub-system may be provided de novo for the HF/IL conversion.

In an embodiment, the ionic liquid specific sub-system may comprise an ionic liquid catalyst alkylation reactor. The ionic liquid catalyst alkylation reactor may be configured for one or more ionic liquid catalyzed hydrocarbon conversion reactions, such as an isoparaffin-olefin alkylation. The ionic liquid catalyst alkylation reactor may also be referred to herein as an ionic liquid alkylation reactor.

In an embodiment, the ionic liquid specific sub-system may further comprise an ionic liquid catalyst/hydrocarbon injection unit, and the method for HF/IL conversion may further comprise connecting the ionic liquid catalyst/hydrocarbon injection unit to at least one hydrocarbon feed line. The ionic liquid catalyst/hydrocarbon injection unit may also be referred to herein as an ionic liquid/hydrocarbon injection unit.

In an embodiment, the ionic liquid/hydrocarbon injection unit may be integral with the ionic liquid alkylation reactor. In an embodiment, at least a portion, e.g., a distal portion, of the ionic liquid/hydrocarbon injection unit may extend into a void or space within the ionic liquid alkylation reactor. In an embodiment, the ionic liquid/hydrocarbon injection unit may be disposed at least partially within the ionic liquid alkylation reactor. In an embodiment, the ionic liquid/hydrocarbon injection unit may be a part or component of the ionic liquid alkylation reactor.

In an embodiment, at least one hydrocarbon feed line may be provided de novo as a component of the ionic liquid alkylation system. In another embodiment, at least one hydrocarbon feed line of the ionic liquid alkylation system may comprise a component from an HF alkylation unit, and the method for HF/IL conversion may comprise disconnecting the HF reactor from the at least one hydrocarbon feed line. Disconnecting the HF reactor from the at least one hydrocarbon feed line or other component(s) may serve to decommission the HF reactor. Thereafter, the HF reactor may be moved, removed, discarded, or may remain in situ, either temporarily or permanently.

In an embodiment of a method for HF/IL conversion, the ionic liquid alkylation reactor may be connected to the at least one hydrocarbon feed line via the ionic liquid/hydrocarbon injection unit. In some embodiments, the ionic liquid alkylation reactor may be supplied with or may include the ionic liquid/hydrocarbon injection unit. At least one hydrocarbon feed may be fed to the ionic liquid alkylation reactor via the at least one hydrocarbon feed line and the ionic liquid/hydrocarbon injection unit. The at least one hydrocarbon feed may be treated, e.g., by a feed treatment unit located upstream from the ionic liquid/hydrocarbon injection unit (see, e.g., FIG. 2).

The method for HF/IL conversion may further comprise connecting the ionic liquid/hydrocarbon injection unit to an ionic liquid catalyst feed line for feeding an ionic liquid catalyst to the ionic liquid alkylation reactor. The ionic liquid catalyst feed line may also be referred to herein as an ionic liquid feed line.

The ionic liquid/hydrocarbon injection unit may be configured for co-injecting the ionic liquid catalyst and at least one hydrocarbon feed into the ionic liquid alkylation reactor. In an embodiment, the ionic liquid/hydrocarbon injection unit may comprise at least one nozzle. The use of one or more nozzles for ionic liquid catalyzed alkylation is disclosed, for example, in commonly assigned U.S. Patent Application Publication Nos. 20090166257, 20090171133, and 20090171134, and in U.S. patent application Ser. No. 12/780,452, filed May 14, 2010, the disclosure of each of which is incorporated by reference herein in its entirety.

In an embodiment, the ionic liquid alkylation reactor and the ionic liquid/hydrocarbon injection unit may be co-configured for forming a mixture comprising an ionic liquid phase and a hydrocarbon phase. Such a mixture may be formed in the ionic liquid alkylation reactor. In an embodiment, said mixture may comprise a dispersed ionic liquid phase and a continuous hydrocarbon phase. As an example, a reaction mixture within the ionic liquid alkylation reactor may comprise an emulsion comprising droplets of ionic liquid catalyst suspended in liquid hydrocarbons. In an embodiment, such droplets may be uniformly suspended in the hydrocarbon phase to provide a homogeneous emulsion. The ionic liquid phase may also be referred to herein as an ionic liquid catalyst phase, it being understood that used ionic liquid catalyst, e.g., downstream from the ionic liquid alkylation reactor, may be at least partially spent or otherwise degraded.

In an embodiment, the ionic liquid alkylation reactor may comprise, or may be used in conjunction with, one or more nozzles for generating the ionic liquid catalyst/hydrocarbon emulsion. In other embodiments, various ionic liquid alkylation reactor configurations may be utilized to provide a uniform or homogeneous mixture of ionic liquid catalyst and hydrocarbon, such as a reactor system containing one or more in-line mixers (e.g., static mixers), or a continuous stirred tank reactor having one or more impellers.

In an embodiment, the ionic liquid specific sub-system may further comprise an ionic liquid catalyst coalescer, and the method for HF/IL conversion may further comprise connecting the ionic liquid catalyst coalescer to a fractionation unit for feeding the hydrocarbon phase to the fractionation unit. The ionic liquid catalyst coalescer may also be referred to herein as an ionic liquid coalescer.

In an embodiment, the fractionation unit of the ionic liquid alkylation system may comprise at least a portion of a conventional fractionation unit from an HF alkylation unit. In an embodiment, the conventional fractionation unit of the HF alkylation unit may be modified, e.g., during an HF/IL conversion, to provide a modified fractionation unit for the ionic liquid alkylation system. In an embodiment, the modified fractionation unit may comprise a portion of the fractionation unit from an HF alkylation unit in combination with one or more fractionation unit components provided de novo for the ionic liquid alkylation system. In an embodiment, the one or more fractionation unit components provided de novo for the ionic liquid alkylation system may comprise a nickel alloy. In an embodiment, one or more components (e.g., comprising carbon steel) of a conventional fractionation unit may be upgraded, e.g., by substituting therefor an alloy such as a Ni/Cu alloy or a Ni/Cr alloy.

It is to be understood that such upgrading of metallurgy is not necessarily limited to the fractionation section of a retrofitted or converted alkylation system. In general, the upgrading of carbon steel components of an existing HF alkylation unit to the higher metallurgy may be performed for streams containing mostly ionic liquid catalyst, such as the ionic liquid catalyst regeneration section and the ionic liquid catalyst recycle line.

In an embodiment, the method for HF/IL conversion may comprise modifying at least one distillation column of the fractionation unit from an HF alkylation unit to provide a retrofitted distillation column for the ionic liquid alkylation system. The retrofitted distillation column may be configured for separating an HCl-rich $C_{3-}$ fraction from the hydrocarbon phase. The ionic liquid alkylation system may be configured for recycling the HCl-rich $C_{3-}$ fraction to the ionic liquid alkylation reactor. Recycling of an HCl- and propane-rich fraction to an ionic liquid alkylation reactor is disclosed in commonly assigned U.S. Patent Application Publication No. 20110155640, the disclosure of which is incorporated by reference herein in its entirety.

In an embodiment, the ionic liquid alkylation system may comprise a primary separator vessel. In an embodiment, the primary separator vessel may be provided de novo for the ionic liquid alkylation system, such that the HF settler from the existing HF alkylation unit may be surplus to requirements for ionic liquid catalyzed alkylation. In which case, a method for HF/IL conversion may comprise disconnecting the HF settler from the fractionation unit. Disconnecting the HF settler from the fractionation unit may serve to decommission the HF settler. The HF settler may be disconnected or decommissioned on a temporary or permanent basis. As non-limiting examples, after disconnecting the HF settler from the fractionation unit, the HF settler may be moved, removed, discarded, or may remain in situ, either temporarily or permanently.

A method for HF/IL conversion of an HF alkylation unit may further comprise connecting the ionic liquid alkylation reactor to the primary separator vessel for feeding an alkylation reactor effluent from the ionic liquid alkylation reactor to the primary separator vessel. The primary separator vessel may be configured for separating the alkylation reactor effluent into a hydrocarbon phase and an ionic liquid phase. In an embodiment, the method for HF/IL conversion may further comprise connecting the primary separator vessel to the ionic liquid coalescer for feeding the hydrocarbon phase from the primary separator vessel to the ionic liquid coalescer.

In an alternative embodiment, the HF settler from an existing or prior HF alkylation unit may be retained and/or adapted as a component of the ionic liquid alkylation system. As an example, the HF settler may be configured for separating alkylation reactor effluent into the hydrocarbon phase and the ionic liquid phase, and the HF settler may serve as, or comprise, the primary separator vessel. In this situation, a method for HF/IL conversion may comprise connecting the ionic liquid alkylation reactor to the HF settler for feeding the alkylation reactor effluent from the ionic liquid alkylation reactor to the HF settler, and connecting the HF settler to the ionic liquid coalescer for feeding the hydrocarbon phase from the HF settler to the ionic liquid coalescer.

According to another embodiment of the present invention, a method for converting an HF alkylation unit to an ionic liquid alkylation system may comprise providing an ionic liquid alkylation reactor and an ionic liquid coalescer, and connecting the ionic liquid alkylation reactor to at least one hydrocarbon feed line and to an ionic liquid feed line via an ionic liquid/hydrocarbon injection unit The ionic liquid/hydrocarbon injection unit may be configured for injecting the ionic liquid catalyst and at least one hydrocarbon feed into the ionic liquid alkylation reactor and for forming, in the ionic liquid alkylation reactor, a homogeneous reaction mixture comprising a dispersed ionic liquid phase and a continuous hydrocarbon phase.

The ionic liquid coalescer may be in fluid communication with the ionic liquid alkylation reactor, e.g., via a primary separator vessel coupled to an outlet port of the ionic liquid alkylation reactor. In an embodiment, the primary separator vessel may comprise an HF settler, and a method for HF/IL conversion may further involve disconnecting the HF settler from the HF reactor, wherein the HF reactor may be decommissioned. In another embodiment, the primary separator vessel may comprise a component provided de novo for the HF/IL conversion, e.g., a component specific to the ionic liquid alkylation system, and a method for HF/IL conversion may further involve disconnecting the HF settler from the fractionation unit, wherein both the HF reactor and the HF settler may be decommissioned.

The ionic liquid coalescer and the primary separator vessel may jointly form an ionic liquid/hydrocarbon separation unit. A method for HF/IL conversion may comprise connecting the primary separator vessel to the ionic liquid alkylation reactor, such that the primary separator vessel may be in fluid communication with the ionic liquid alkylation reactor for feeding an alkylation reactor effluent from the ionic liquid reactor to the primary separator vessel. The primary separator vessel may be configured for separating the alkylation reactor effluent into a hydrocarbon phase and an ionic liquid phase.

The ionic liquid coalescer may receive at least a portion of the hydrocarbon phase from the primary separator vessel. In an embodiment, the hydrocarbon phase from the primary separator vessel may be incompletely separated from the ionic liquid; for example, the hydrocarbon phase from the primary separator vessel may comprise entrained ionic liquid. The ionic liquid coalescer may be configured for separating the entrained ionic liquid from the hydrocarbon phase, and the ionic liquid alkylation system may be configured for recycling the entrained ionic liquid from the ionic liquid coalescer to the ionic liquid alkylation reactor.

In an embodiment, a method for HF/IL conversion may further comprise connecting the ionic liquid coalescer to the fractionation unit. The fractionation unit may be retained from the existing HF alkylation unit undergoing conversion, or may be derived or adapted from one or more components of the fractionation unit of said HF alkylation unit.

An HF alkylation unit destined for conversion to an ionic liquid alkylation system may include at least one component comprising a material, e.g., carbon steel, which is incompatible with one or more zones of ionic liquid catalyzed alkylation processes. In an embodiment, a method for HF/IL conversion may comprise replacing one or more component(s) of the HF alkylation unit with one or more component(s) comprising a suitable material, e.g., a nickel alloy. In a sub-embodiment, the Ni alloy may comprise a Ni/Cr alloy comprising predominantly Ni (>50 wt % Ni) in combination with up to about 26 wt % Cr. In another sub-embodiment, the Ni alloy may comprise a Ni/Cu alloy comprising predominantly Ni (>50 wt % Ni) in combination with up to about 32 wt % Cu. Non-limiting examples of a Ni/Cr alloy and a Ni/Cu alloy are Alloy C-276 and Alloy 400, respectively.

According to another embodiment, an HF alkylation unit for conversion to an ionic liquid alkylation system may include an HF reactor, an HF settler disposed downstream from the HF reactor, and a fractionation unit disposed downstream from the HF settler. A method for converting the HF alkylation unit to the ionic liquid alkylation system may comprise providing an ionic liquid alkylation reactor configured for ionic liquid catalyzed alkylation reactions. The ionic liquid alkylation reactor may have an ionic liquid/hydrocarbon injection unit in fluid communication therewith. In an embodiment, the ionic liquid/hydrocarbon injection unit may be integral with, disposed within, and/or a component of the ionic liquid alkylation reactor.

In another embodiment, a method for HF/IL conversion may comprise configuring the ionic liquid/hydrocarbon injection unit for co-injecting the ionic liquid catalyst and at least one hydrocarbon feed into the ionic liquid alkylation reactor. In an embodiment, the ionic liquid alkylation reactor and the ionic liquid/hydrocarbon injection unit may be co-configured for forming, in the ionic liquid alkylation reactor, a homogeneous mixture comprising a dispersed ionic liquid phase and a continuous hydrocarbon phase.

The ionic liquid/hydrocarbon injection unit may be connected to at least one hydrocarbon feed line for feeding at least one hydrocarbon feed to the ionic liquid alkylation reactor. In an embodiment, the at least one hydrocarbon feed may be treated via a feed treatment unit disposed upstream from the ionic liquid/hydrocarbon injection unit.

In an embodiment, the at least one hydrocarbon feed may comprise an isoparaffin containing feed and an olefin containing feed. The feed treatment unit may comprise at least one feed dryer unit for drying the hydrocarbon feed(s). The feed treatment unit may further comprise a hydroisomerization unit for treating an olefin containing feed, e.g., for removing butadiene and for isomerizing 1-butene to 2-butene.

In an embodiment, the feed treatment unit may comprise a component of an existing or prior HF alkylation unit. In another embodiment, an existing HF alkylation unit for conversion to an ionic liquid alkylation system may lack a suitable feed treatment unit, and the feed treatment unit for the ionic liquid alkylation system may comprise one or more components provided de novo for the HF/IL conversion.

During an HF/IL conversion the ionic liquid/hydrocarbon separation unit may be connected to the ionic liquid alkylation reactor. The ionic liquid/hydrocarbon separation unit may be configured for separating an alkylation reactor effluent of the ionic liquid alkylation reactor into the ionic liquid phase and the hydrocarbon phase. The ionic liquid phase may comprise ionic liquid catalyst, while the hydrocarbon phase may comprise an alkylate. The hydrocarbon phase may further comprise unconverted light hydrocarbons.

The ionic liquid/hydrocarbon separation unit may comprise a primary separator vessel and an ionic liquid coalescer in fluid communication with the primary separator vessel. In an embodiment, the ionic liquid/hydrocarbon separation unit may be connected to the ionic liquid alkylation reactor via the primary separator vessel. In an embodiment, the primary separator vessel may comprise the HF settler.

A method for HF/IL conversion may further comprise connecting the ionic liquid/hydrocarbon separation unit to the fractionation unit for feeding at least a portion of the hydrocarbon phase to the fractionation unit. In an embodiment, the ionic liquid/hydrocarbon separation unit may be connected to the fractionation unit via the ionic liquid coalescer.

The method for HF/IL conversion may further comprise providing an ionic liquid catalyst regeneration unit for regenerating the ionic liquid catalyst, and connecting the ionic liquid catalyst regeneration unit to the ionic liquid/hydrocarbon separation unit for feeding a portion of the ionic liquid phase from the ionic liquid/hydrocarbon separation unit to the ionic liquid catalyst regeneration unit. The ionic liquid phase from the ionic liquid/hydrocarbon separation unit may comprise at least partially spent ionic liquid catalyst, and the ionic liquid/hydrocarbon separation unit may be configured for regenerating such ionic liquid catalyst to provide regenerated ionic liquid catalyst.

The method for HF/IL conversion may further comprise connecting the ionic liquid catalyst regeneration unit to the ionic liquid alkylation reactor for feeding at least a portion of the regenerated ionic liquid catalyst to the ionic liquid alkylation reactor. The regeneration of ionic liquid catalysts is disclosed, for example, in commonly assigned U.S. Pat. Nos. 7,674,739 and 7,691,771, the disclosure of each of which is incorporated by reference herein in its entirety.

After an HF/IL conversion has been completed, the resulting ionic liquid alkylation system may begin operation following a suitable startup procedure. Methods for starting and operating ionic liquid catalyzed hydrocarbon conversion processes and systems are disclosed in commonly assigned, co-pending U.S. patent application Ser. No. 12/825,121, filed Jun. 28, 2010, the disclosure of which is incorporated by reference herein in its entirety.

Ionic Liquid Catalyzed Alkylation Processes

Figure 2:
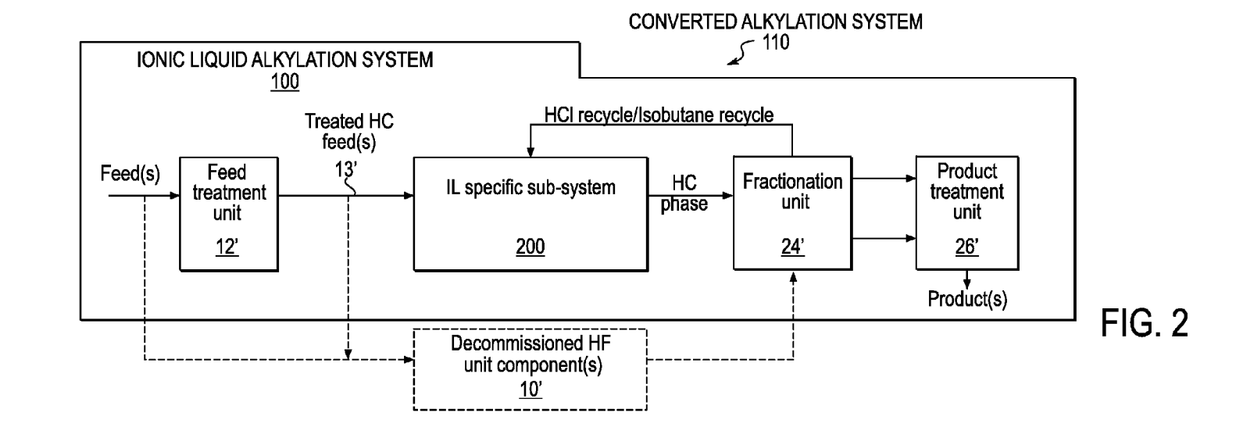
FIG. 2 schematically represents a converted ionic liquid catalyzed alkylation system, according to an embodiment of the present invention.
Figure 3:
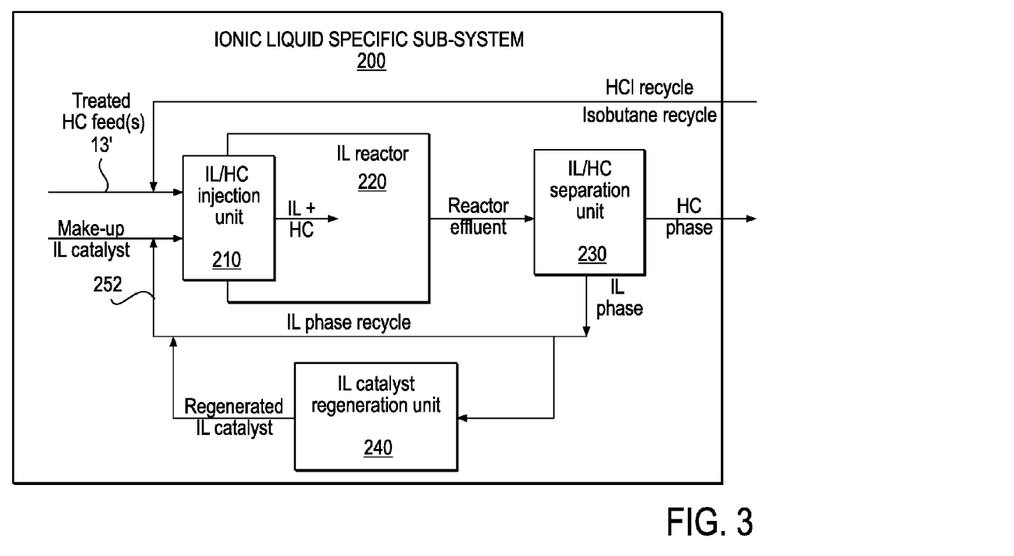
FIG. 3 schematically represents a sub-system for an ionic liquid alkylation system, according to another embodiment of the present invention.
Figure 4:
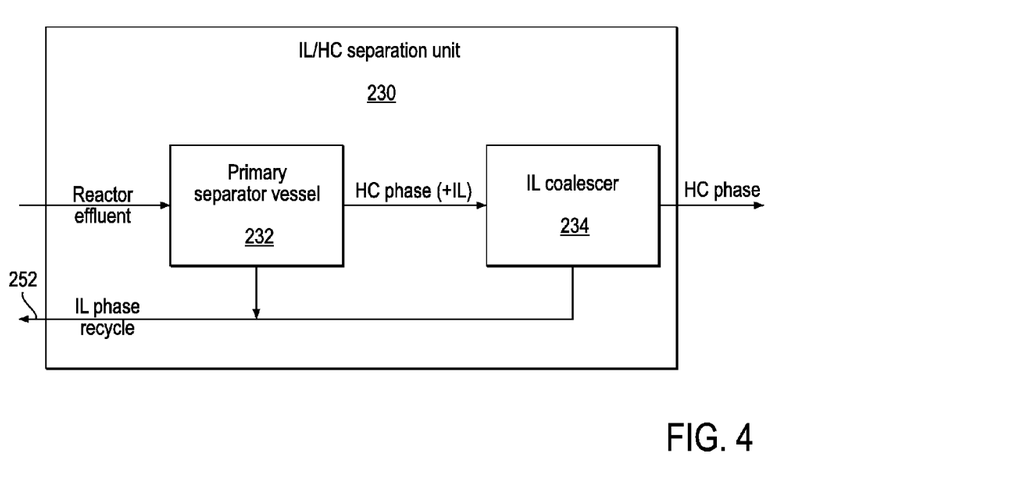
FIG. 4 schematically represents an ionic liquid catalyst/hydrocarbon separation unit for an ionic liquid catalyzed alkylation system, according to another embodiment of the present invention.

With reference to FIGS. 2-4, during an ionic liquid catalyzed alkylation process conducted using system 100, treated hydrocarbon feed(s) may be introduced into ionic liquid alkylation reactor 220. Ionic liquid alkylation reactor 220 may also be referred to herein as an ionic liquid alkylation zone. The hydrocarbon feed(s) may be treated using feed treatment unit 12'. The hydrocarbon feed(s) may include at least one hydrocarbon reactant. In a sub-embodiment, the at least one hydrocarbon reactant may comprise a first reactant comprising a $C_4$-$C_{10}$ isoparaffin and a second reactant comprising a $C_2$-$C_{10}$ olefin. Treatment of the hydrocarbon feed(s) may include feed drying, as well as the removal of dienes and the hydroisomerization of olefins in olefin feeds. The selective hydrogenation and hydroisomerization of feedstock for ionic liquid catalyzed alkylation is disclosed in commonly assigned U.S. Patent Application Publication No. 20110092753, the disclosure of which is incorporated by reference herein in its entirety.

Ionic liquid catalyst and the at least one hydrocarbon feed may be introduced into ionic liquid alkylation reactor 220 via ionic liquid/hydrocarbon injection unit 210. In an embodiment, the ionic liquid catalyst may comprise a chloroaluminate ionic liquid, as described hereinbelow. A co-catalyst such as anhydrous HCl and/or a catalyst promoter may also be fed to ionic liquid alkylation reactor 220. Ionic liquid/hydrocarbon injection unit 210 may also be referred to herein as an ionic liquid catalyst/hydrocarbon injection unit 210.

One skilled in the art will recognize that FIGS. 2-4 are schematic representations indicating fluid communication between units or components. FIGS. 2-4 are not intended to show relative size, shape, or spatial relationships between components or units. For example, in an embodiment ionic liquid/hydrocarbon injection unit 210 may be integral with ionic liquid alkylation reactor 220. In an embodiment, at least a portion, e.g., a distal portion, of ionic liquid/hydrocarbon injection unit 210 may extend into a void or space within ionic liquid alkylation reactor 220. In an embodiment, ionic liquid/hydrocarbon injection unit 210 may be disposed at least partially within ionic liquid alkylation reactor 220. In an embodiment, ionic liquid/hydrocarbon injection unit 210 may be a part or component of ionic liquid alkylation reactor 220.

During alkylation processes according to embodiments of the invention, ionic liquid alkylation reactor 220 may contain a biphasic mixture comprising an ionic liquid phase and a hydrocarbon phase. The hydrocarbon phase may comprise at least one hydrocarbon product of the ionic liquid catalyzed reaction. The ionic liquid phase may be separated from the hydrocarbon phase via ionic liquid/hydrocarbon separation unit 230. Ionic liquid/hydrocarbon separation unit 230 may also be referred to herein as an ionic liquid catalyst/hydrocarbon separation unit 230. Ionic liquid/hydrocarbon separation unit 230 may comprise a primary separator vessel 232 and an ionic liquid coalescer 234. Ionic liquid coalescer 234 may also be referred to herein as an ionic liquid catalyst coalescer 234.

In an embodiment, at least a portion of the ionic liquid phase from ionic liquid/hydrocarbon separation unit 230 may be recycled to ionic liquid alkylation reactor 220. With continued operation of system 100, the ionic liquid catalyst may become at least partially deactivated. In order to maintain catalytic activity of the ionic liquid catalyst, a portion of the ionic liquid catalyst phase may be fed to ionic liquid catalyst regeneration unit 230 for regeneration of the ionic liquid catalyst. Thereafter, at least a portion of the regenerated ionic liquid catalyst may be recycled to ionic liquid alkylation reactor 220, e.g., via an ionic liquid feed line 252 and ionic liquid/hydrocarbon injection unit 210.

In an embodiment, at least a portion of the hydrocarbon phase from ionic liquid coalescer 234 may be fed to fraction- ation unit 24' for fractionation of the hydrocarbon phase to provide one or more hydrocarbon products. The one or more hydrocarbon products may be fed to product treatment unit 26' for treating the hydrocarbon product(s). In an embodiment, fractionation unit 24', which may include multiple distillation or fractionation columns, may comprise a modified fractionation unit obtained by modifying fractionation unit 24 of conventional alkylation unit 10 (FIG. 1). Fractionation unit 24' may comprise at least one converted, modified or retrofitted distillation column that is configured for the separation of an HCl-rich $C_{3-}$ fraction. At least a portion of the HCl-rich $C_{3-}$ fraction may be recycled to ionic liquid alkylation reactor 220. At least one fraction comprising isobutane may also be recycled to ionic liquid alkylation reactor 220. For the sake of clarity, only a single line is shown for recycling HCl— and isobutane containing fractions to ionic liquid alkylation reactor 220.

Ionic Liquid Catalysts

Ionic liquids are generally organic salts with melting points below 100° C. (212° F.) and often below room temperature. They may find applications in various chemical reactions, solvent processes, and electrochemistry. The use of chloroaluminate ionic liquids as alkylation catalysts in petroleum refining has been described, for example, in commonly assigned U.S. Pat. Nos. 7,531,707, 7,569,740, and 7,732,654, the disclosure of each of which is incorporated by reference herein in its entirety.

Most ionic liquids are prepared from organic cations and inorganic or organic anions. Cations include, but are not limited to, ammonium, phosphonium and sulphonium. Anions include, but are not limited to, $BE_4^-$, $PF_6^-$, haloaluminates such as $Al_2Cl_7^-$ and $Al_2Br_7^-$, $[(CF_3SO_2)_2N]^-$, alkyl sulfates ($RSO_3^-$), and carboxylates ($RCO_2^-$). Ionic liquids for acid catalysis may include those derived from ammonium halides and Lewis acids, such as $AlCl_3$, $TiCl_4$, $SnCl_4$, and $FeCl_3$. Chloroaluminate ionic liquids are perhaps the most commonly used ionic liquid catalyst systems for acid catalyzed reactions.

Exemplary ionic liquids for use as catalysts in ionic liquid catalyzed alkylation reactions may comprise at least one compound of the general formulas A and B:

wherein R is selected from the group consisting of H, methyl, ethyl, propyl, butyl, pentyl or hexyl, each of $R_1$ and $R_2$ is selected from the group consisting of H, methyl, ethyl, propyl, butyl, pentyl or hexyl, wherein $R_1$ and $R_2$ may or may not be the same, and X is a chloroaluminate.

Non-limiting examples of chloroaluminate ionic liquid catalysts that may be used in alkylation processes according to embodiments of the instant invention include those comprising 1-butyl-4-methyl-pyridinium chloroaluminate, 1-butyl-3-methyl-imidazolium chloroaluminate, 1-H-pyridinium chloroaluminate, N-butylpyridinium chloroaluminate, and mixtures thereof.

Reaction Conditions for Ionic Liquid Catalyzed Hydrocarbon Conversion Reactions

Due to the low solubility of hydrocarbons in ionic liquids, hydrocarbon conversion reactions in ionic liquids (including isoparaffin-olefin alkylation reactions) are generally biphasic and occur at the interface in the liquid state. The volume of ionic liquid catalyst in the reactor may be generally in the range from about 1 to 70 vol %, and usually from about 4 to 50 vol %. In an embodiment, an ionic liquid/hydrocarbon injection unit may be used to co-inject reactant(s) and ionic liquid catalyst into the ionic liquid alkylation reactor to ensure good contact between the ionic liquid catalyst and reactants.

The reaction temperature may be generally in the range from about −40 to +250° C. (−40 to +482° F.), typically from about −20 to +100° C. (−4 to +212° F.), and often from about +4 to +60° C. (+40 to +140° F.). The reactor pressure may be in the range from atmospheric pressure to about 8000 kPa. Typically, the reactor pressure is sufficient to keep the reactants in the liquid phase.

Residence time of reactants in the reactor may generally be in the range from a few seconds to hours, and usually from about 0.5 min to 60 min. In the case of ionic liquid catalyzed isoparaffin-olefin alkylation, the reactants may be introduced in an isoparaffin:olefin molar ratio generally in the range from about 1-100, more typically from about 2-50, and often from about 2-20. Heat generated by the reaction may be dissipated using various means well known to the skilled artisan. Reactor conditions may be adjusted to optimize process performance for a particular ionic liquid catalyzed alkylation process.

Ionic Liquid Alkylation Systems Derived from HF Alkylation Units

In an embodiment, the present invention provides an ionic liquid alkylation system configured for performing ionic liquid alkylation processes, wherein said system may be derived from an existing or prior HF alkylation unit. As an example, one or more components of an ionic liquid alkylation system according to embodiments of the present invention may be provided by, or derived or adapted from, an existing or prior HF alkylation unit.

FIG. 2 schematically represents a converted ionic liquid catalyzed alkylation system, according to an embodiment of the present invention. Converted ionic liquid catalyzed alkylation system 110 may comprise an ionic liquid alkylation system 100. In an embodiment, converted ionic liquid catalyzed alkylation system 110 may further comprise one or more decommissioned HF unit components 10'. By "decommissioned HF unit components" is meant one or more components of HF alkylation unit 10 that are taken out of service, either temporarily or permanently. Ionic liquid alkylation system 100 may also be referred to herein as ionic liquid catalyst alkylation system 100.

The one or more decommissioned HF unit components 10' may be disconnected from one or more retained components of HF alkylation unit 10. By "retained components" of HF alkylation unit 10' is meant one or more components from HF alkylation unit 10 that are to be retained, either as is or in modified form, for performing ionic liquid catalyzed alkylation processes.

In an embodiment, one or more decommissioned HF unit components 10' may remain in situ, e.g., adjacent to one or more ionic liquid specific components of ionic liquid alkylation system 100. In another embodiment, one or more decommissioned HF unit components 10' may be removed and/or discarded. As an example, decommissioned HF unit component(s) 10' may comprise HF reactor 16 (FIG. 1). As another example, decommissioned HF unit component(s) 10' may comprise HF reactor 16 and HF settler 18. As a further example, decommissioned HF unit component(s) 10' may comprise HF reactor 16, HF settler 18 and HF regeneration unit 22.

With reference to FIGS. 2 and 3, ionic liquid alkylation system 100 may comprise a feed treatment unit 12', at least one hydrocarbon feed line 13', an ionic liquid specific sub-system 200, a fractionation unit 24', and a product treatment unit 26'. Ionic liquid alkylation system 100 may be used for efficiently conducting an ionic liquid catalyzed alkylation process. Feed treatment unit 12' may be configured for treating at least one hydrocarbon feed for ionic liquid catalyzed alkylation reactions. Fractionation unit 24' may be configured for fractionating the hydrocarbon phase from ionic liquid alkylation reactor 220 to provide one or more hydrocarbon products, and for separating HCl and isobutane for recycling to ionic liquid specific sub-system 200. One or more of the hydrocarbon products may be fed to product treatment unit 26' for removing any contaminants from the hydrocarbon product(s). In an embodiment, the HCl may be separated, and recycled to ionic liquid specific sub-system 200, as an HCl-rich $C_{3-}$ fraction.

In an embodiment, at least one component of an existing HF alkylation unit may be retained, at least temporarily, for use in ionic liquid alkylation system 100. Such retained component(s) may include, for example, one or more of feed treatment unit 12', hydrocarbon feed line 13', fractionation unit 24', and product treatment unit 26'. In another embodiment, one or more components selected from feed treatment unit, 12', hydrocarbon feed line 13', fractionation unit 24', and product treatment unit 26' may be provided de novo, e.g., specifically for assembling ionic liquid alkylation system 100.

In another embodiment, one or more components of ionic liquid alkylation system 100 selected from feed treatment unit 12', hydrocarbon feed line 13', fractionation unit 24', and product treatment unit 26' may comprise an adapted, retrofitted or modified unit or component from a prior HF alkylation unit. As a non-limiting example, a conventional fractionation unit 24 may be modified to provide a modified fractionation unit 24' configured for separating an HCl-rich $C_{3-}$ fraction from the hydrocarbon phase. Ionic liquid alkylation system 100 may be configured or adapted, e.g., during an HF/IL conversion, for recycling the HCl-rich $C_{3-}$ fraction to ionic liquid alkylation reactor 220.

FIG. 3 schematically represents an ionic liquid specific sub-system for an ionic liquid alkylation system, according to an embodiment of the present invention. Ionic liquid specific sub-system 200 may comprise an ionic liquid/hydrocarbon injection unit 210, an ionic liquid alkylation reactor 220, an ionic liquid/hydrocarbon separation unit 230, an ionic liquid catalyst regeneration unit 240, and ionic liquid catalyst feed line 252.

At least one treated hydrocarbon feed may be fed to ionic liquid alkylation reactor 220 via hydrocarbon feed line 13' and ionic liquid/hydrocarbon injection unit 210. At the same time, ionic liquid catalyst may be fed to ionic liquid alkylation reactor 220 via ionic liquid feed line 252 and ionic liquid/hydrocarbon injection unit 210. Ionic liquid/hydrocarbon injection unit 210 may be connected to, and in fluid communication with, ionic liquid alkylation reactor 220, for injecting an ionic liquid/hydrocarbon mixture into ionic liquid alkylation reactor 220. In an embodiment, ionic liquid/hydrocarbon injection unit 210 may be integral with, disposed within, or a component of ionic liquid alkylation reactor 220.

Ionic liquid/hydrocarbon injection unit 210 may include at least one nozzle (not shown). Nozzles for introducing ionic liquid catalyst and hydrocarbon feeds into an ionic liquid alkylation reactor are disclosed in commonly assigned U.S. Patent Application Publication Nos. 20090166257, 20090171133, and 20090171134, and in U.S. patent application Ser. No. 12/780,452, filed May 14, 2010, the disclosure of each of which is incorporated by reference herein in its entirety.

Ionic liquid alkylation reactor 220 may be configured for ionic liquid catalyzed alkylation reactions. The mixture in ionic liquid alkylation reactor 220 may comprise an ionic liquid phase and a hydrocarbon phase. The mixture in ionic liquid alkylation reactor 22 may comprise a reaction emulsion. The emulsion may comprise a homogeneously dispersed ionic liquid phase in a continuous hydrocarbon phase.

FIG. 4 schematically represents an ionic liquid/hydrocarbon separation unit for an ionic liquid catalyzed alkylation system, according to an embodiment of the present invention. Ionic liquid/hydrocarbon separation unit 230 may include a primary separator vessel 232 and an ionic liquid coalescer 234.

With further reference to FIGS. 3 and 4, ionic liquid/hydrocarbon separation unit 230 may be connected to ionic liquid alkylation reactor 220 via primary separator vessel 232. Primary separator vessel 232 may be configured for receiving alkylation reactor effluent from ionic liquid alkylation reactor 220, and for separating the alkylation reactor effluent into a hydrocarbon phase and an ionic liquid phase. In an embodiment, the primary separator vessel 232 may comprise the HF settler from an HF alkylation unit undergoing or having undergone an HF/IL conversion.

At least a first portion of the ionic liquid phase from primary separator vessel 232 may be recycled to ionic liquid alkylation reactor 220. A second portion of the ionic liquid phase from ionic liquid/hydrocarbon separation unit 230 may be fed to ionic liquid catalyst regeneration unit 240 for ionic liquid catalyst regeneration, and regenerated ionic liquid catalyst may be recycled to ionic liquid alkylation reactor 220.

Ionic liquid coalescer 234 may be connected to, and in fluid communication with, primary separator vessel 232 for receiving at least a portion of the hydrocarbon phase from primary separator vessel 232. Ionic liquid coalescer 234 may be configured for separating any entrained ionic liquid from the hydrocarbon phase. The entrained ionic liquid may be recycled from the ionic liquid coalescer 234 to ionic liquid alkylation reactor 220.

In an embodiment, ionic liquid coalescer 234 may comprise multiple stages or modules of coalescer material, and the stages may be arranged in series and/or in parallel. The coalescer material may be selected to have a higher affinity for the ionic liquid phase as compared with the hydrocarbon phase, and the coalescer material may be fully wettable by the ionic liquid phase. The separation of an ionic liquid/hydrocarbon emulsion using a coalescer is disclosed in commonly assigned U.S. Patent Application Publication No. 20100130800, the disclosure of which is incorporated by reference herein in its entirety.

There are numerous variations on the present invention which are possible in light of the teachings herein. It is therefore understood that within the scope of the following claims, the invention may be practiced otherwise than as specifically described or exemplified herein.

What is claimed is:

1. A method for converting an HF alkylation unit which includes an HF settler to an ionic liquid alkylation system, the method comprising:

a) providing an ionic liquid specific sub-system comprising an ionic liquid alkylation reactor and an ionic liquid coalescer;
b) connecting the ionic liquid alkylation reactor to the HF settler for feeding an alkylation reactor effluent from the ionic liquid alkylation reactor to the HF settler, wherein the HF settler is configured for separating the alkylation reactor effluent into a hydrocarbon phase and an ionic liquid phase; and
c) connecting the HF settler to the ionic liquid coalescer for feeding the hydrocarbon phase from the HF settler to the ionic liquid coalescer, wherein the alkylation reactor effluent is a homogeneous emulsion.

2. The method according to claim 1, wherein the ionic liquid specific sub-system further comprises an ionic liquid/hydrocarbon injection unit in fluid communication with the ionic liquid alkylation reactor, and the method further comprising:
d) connecting the ionic liquid/hydrocarbon injection unit to at least one hydrocarbon feed line, wherein the ionic liquid alkylation reactor and the ionic liquid/hydrocarbon injection unit are co-configured for forming a mixture comprising an ionic liquid phase and a hydrocarbon phase.

3. The method according to claim 1, wherein the HF alkylation unit includes an HF settler and a fractionation unit disposed downstream from the HF settler, the ionic liquid specific sub-system further comprises a primary separator vessel, and the method further comprising:
e) disconnecting the HF settler from the fractionation unit;
f) connecting the ionic liquid alkylation reactor to the primary separator vessel for feeding an alkylation reactor effluent from the ionic liquid alkylation reactor to the primary separator vessel, wherein the primary separator vessel is configured for separating the alkylation reactor effluent into a hydrocarbon phase and an ionic liquid phase.

4. The method according to claim 3, wherein the ionic liquid specific sub-system further comprises an ionic liquid coalescer, and the method further comprising:
g) connecting the primary separator vessel to the ionic liquid coalescer for feeding the hydrocarbon phase from the primary separator vessel to the ionic liquid coalescer; and
h) connecting the ionic liquid coalescer to the fractionation unit for feeding the hydrocarbon phase from the ionic liquid coalescer to the fractionation unit.

5. The method according to claim 1, wherein the HF alkylation unit includes a fractionation unit, and the method further comprising:
i) modifying the fractionation unit to provide a modified fractionation unit such that the modified fractionation unit is configured for separating an HCl-rich $C_3$-fraction from the hydrocarbon phase for recycling to the alkylation unit.

6. The method according to claim 1, further comprising:
j) replacing at least one component of the HF alkylation unit with a component comprising a Ni/Cr alloy or a Ni/Cu alloy.

7. A method for converting an HF alkylation unit to an ionic liquid alkylation system, the HF alkylation unit including a fractionation unit, an HF reactor, and an HF settler disposed downstream from the HF reactor and upstream from the fractionation unit, and the method comprising:
a) providing an ionic liquid alkylation reactor and an ionic liquid coalescer;
b) connecting the ionic liquid alkylation reactor to at least one hydrocarbon feed line for feeding at least one hydrocarbon feed to the ionic liquid alkylation reactor;
c) connecting the ionic liquid coalescer to the fractionation unit
d) providing an ionic liquid/hydrocarbon injection unit, wherein step b) comprises connecting the ionic liquid alkylation reactor to the at least one hydrocarbon feed line via the ionic liquid/hydrocarbon injection unit and wherein the ionic liquid alkylation reactor and the ionic liquid/hydrocarbon injection unit are co-configured for forming a mixture comprising a dispersed ionic liquid phase and a continuous hydrocarbon phase;
e) disconnecting the HF settler from the HF reactor;
f) connecting the HF settler to the ionic liquid alkylation reactor, wherein the HF settler is in fluid communication with the ionic liquid alkylation reactor for feeding an alkylation reactor effluent from the ionic liquid alkylation reactor to the HF settler, and the HF settler is configured for separating the alkylation reactor effluent into a hydrocarbon phase and an ionic liquid phase; and
g) connecting the HF settler to the ionic liquid coalescer, wherein the alkylation reactor effluent is a homogeneous emulsion.

8. The method according to claim 7, further comprising:
h) connecting the ionic liquid/hydrocarbon injection unit to an ionic liquid feed line, wherein the ionic liquid/hydrocarbon injection unit is configured for injecting an ionic liquid catalyst and at least one hydrocarbon feed into the ionic liquid alkylation reactor.

9. The method according to claim 7, further comprising:
i) providing a primary separator vessel; and
j) connecting the primary separator vessel to the ionic liquid coalescer.

10. The method according to claim 9, further comprising:
k) connecting the primary separator vessel to the ionic liquid alkylation reactor, wherein the primary separator vessel is in fluid communication with the ionic liquid alkylation reactor for feeding an alkylation reactor effluent from the ionic liquid alkylation reactor to the primary separator vessel, and the primary separator vessel is configured for separating the alkylation reactor effluent into a hydrocarbon phase and an ionic liquid phase.

11. The method according to claim 10, wherein:
the HF alkylation unit further includes an HF reactor, and an HF settler disposed downstream from the HF reactor and upstream from the fractionation unit, and the method further comprising:
l) providing the HF reactor from at least one hydrocarbon feed line; and
m) connecting the HF settler from the fractionation unit.

12. The method according to claim 7, wherein an alkylation reactor effluent from the ionic liquid alkylation reactor comprises a hydrocarbon phase, and the method further comprising:
n) modifying the fractionation unit to provide a modified fractionation unit such that the modified fractionation unit is configured for separating an HCl-rich $C_3$-fraction from the hydrocarbon phase, wherein the ionic liquid alkylation system is configured for recycling the HCl-rich $C_3$-fraction to the ionic liquid alkylation reactor.

13. A method for converting an HF alkylation unit to an ionic liquid alkylation system, the HF alkylation unit including a fractionation unit, and the method comprising:
a) providing an ionic liquid alkylation reactor configured for ionic liquid catalyzed alkylation reactions, the ionic liquid alkylation reactor having an ionic liquid/hydrocarbon injection unit in fluid communication therewith;

b) connecting at least one hydrocarbon feed line to the ionic liquid/hydrocarbon injection unit for feeding at least one hydrocarbon feed to the ionic liquid alkylation reactor;

c) providing an ionic liquid/hydrocarbon separation unit;

d) connecting the ionic liquid/hydrocarbon separation unit to the ionic liquid alkylation reactor, wherein the ionic liquid/hydrocarbon separation unit is configured for separating an alkylation reactor effluent of the ionic liquid alkylation reactor into an ionic liquid phase comprising an ionic liquid catalyst and a hydrocarbon phase comprising alkylate;

e) connecting the ionic liquid/hydrocarbon separation unit to the fractionation unit for feeding at least a portion of the hydrocarbon phase to the fractionation unit; and f) modifying the fractionation unit to provide a modified fractionation unit such that the modified fractionation unit is configured for separating an HCl-rich C3-fraction from the hydrocarbon phase, and the ionic liquid alkylation system is configured for recycling the HCl-rich C3-fraction to the ionic liquid alkylation reactor, wherein the alkylation reactor effluent is a homogeneous emulsion.

14. The method according to claim 13, further comprising:

g) providing an ionic liquid catalyst regeneration unit, wherein the ionic liquid alkylation system is configured for recycling regenerated ionic liquid catalyst from the ionic liquid catalyst regeneration unit to the ionic liquid alkylation reactor.

15. The method according to claim 13, wherein:

the ionic liquid/hydrocarbon separation unit comprises a primary separator vessel and an ionic liquid coalescer in fluid communication with the primary separator vessel, and wherein:

step d) comprises connecting the primary separator vessel to the ionic liquid alkylation reactor, and step e) comprises connecting the ionic liquid coalescer to the fractionation unit.

16. The method according to claim 15, wherein:

the HF alkylation unit further includes an HF settler, and the primary separator vessel comprises the HF settler.

* * * * *